US010790058B2

(12) United States Patent
Keegan et al.

(10) Patent No.: US 10,790,058 B2
(45) Date of Patent: *Sep. 29, 2020

(54) USER INSTALLED APPLICATIONS IN A PHYSIOLOGICAL PARAMETER DISPLAY DEVICE

(71) Applicant: Welch Allyn, Inc., Skaneateles Falls, NY (US)

(72) Inventors: Christopher M. Keegan, Marcellus, NY (US); Frank LoMascolo, Auburn, NY (US); Kenzi Mudge, Skaneateles Falls, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 546 days.

This patent is subject to a terminal disclaimer.

(21) Appl. No.: 15/424,025

(22) Filed: Feb. 3, 2017

(65) Prior Publication Data
US 2017/0147192 A1 May 25, 2017

Related U.S. Application Data

(63) Continuation of application No. 13/817,185, filed as application No. PCT/US2010/045814 on Aug. 17, 2010, now Pat. No. 9,600,630.

(51) Int. Cl.
*G16H 40/63* (2018.01)
*G06F 19/00* (2018.01)
(Continued)

(52) U.S. Cl.
CPC .......... *G16H 40/63* (2018.01); *G06F 3/0482* (2013.01); *G06F 3/04817* (2013.01);
(Continued)

(58) Field of Classification Search
None
See application file for complete search history.

(56) References Cited

U.S. PATENT DOCUMENTS

| 5,473,536 A | 12/1995 | Wimmer |
| 6,175,877 B1 * | 1/2001 | Zerber ...................... G06F 9/54 709/203 |

(Continued)

FOREIGN PATENT DOCUMENTS

| KR | 10-2009-0049566 A | 5/2009 |
| WO | 2006/136972 A1 | 12/2006 |

OTHER PUBLICATIONS

International Search Report for PCT/US2010/045814 dated Mar. 30, 2011, 8pgs.
Tunes, publisher: apple.com, publication date: Mar. 19, 2010.

*Primary Examiner* — Abdullah Al Kawsar
*Assistant Examiner* — David V Luu
(74) *Attorney, Agent, or Firm* — Merchant & Gould P.C.

(57) ABSTRACT

A physiological parameter display device displays data representing the current values of one or more physiological parameters of a patient. The device has an operating system that does not allow multiple-program execution. A program runs on the operating system. The program provides functionality that gives a user of the device an ability to install virtual applications on the device. In addition, the program provides functionality that gives the user an ability to run the virtual applications on the device while the device continues to display data representing the current value of the physiological parameter of the patient.

19 Claims, 10 Drawing Sheets

(51) Int. Cl.
*G16H 40/40* (2018.01)
*G06F 3/0481* (2013.01)
*G06F 3/0482* (2013.01)
*G06F 3/0484* (2013.01)

(52) U.S. Cl.
CPC .......... *G06F 3/04847* (2013.01); *G06F 19/00* (2013.01); *G06F 19/3418* (2013.01); *G16H 40/40* (2018.01)

(56) References Cited

U.S. PATENT DOCUMENTS

| | | | |
|---|---|---|---|
| 2004/0054718 A1* | 3/2004 | Hicks, III | H04L 67/125 709/203 |
| 2005/0066202 A1 | 3/2005 | Evans et al. | |
| 2005/0242942 A1 | 11/2005 | Staats et al. | |
| 2005/0251806 A1 | 11/2005 | Auslander | |
| 2006/0149597 A1 | 7/2006 | Powell et al. | |
| 2006/0155589 A1 | 7/2006 | Lane et al. | |
| 2007/0010721 A1 | 1/2007 | Chen et al. | |
| 2007/0288912 A1* | 12/2007 | Zimmer | G06F 9/5027 717/148 |
| 2008/0059592 A1 | 3/2008 | Marsh | |
| 2008/0244057 A1* | 10/2008 | Kojima | G06F 8/61 709/223 |
| 2009/0112072 A1* | 4/2009 | Banet | A61B 5/0205 600/301 |
| 2009/0307105 A1* | 12/2009 | Lemay | G06F 8/61 705/26.1 |
| 2010/0058337 A1* | 3/2010 | Lloyd | G06F 9/526 718/1 |
| 2010/0152600 A1 | 6/2010 | Droitcour et al. | |
| 2010/0223613 A1* | 9/2010 | Schneider | G06F 9/45558 718/1 |
| 2011/0001605 A1 | 1/2011 | Kiani et al. | |
| 2011/0093402 A1* | 4/2011 | Gupta | G06F 21/10 705/317 |
| 2011/0138386 A1* | 6/2011 | Davis | G16H 40/63 718/1 |
| 2011/0227739 A1* | 9/2011 | Gilham | G16H 40/63 340/573.1 |
| 2011/0258301 A1 | 10/2011 | McCormick et al. | |

\* cited by examiner

USER INSTALLED APPLICATIONS IN A PHYSIOLOGICAL PARAMETER DISPLAY DEVICE

BACKGROUND

Physiological parameter display devices are used in a variety of clinical settings to help caregivers learn various physiological parameters of patients. For example, a physiological parameter display device can be used in an operating room to monitor a patient's pulse rate, blood oxygen saturation level, body temperature, and blood pressure. In another example, a physiological parameter display devices can be used to spot check physiological parameters of patients.

In many cases, physiological parameter display devices use embedded operating systems to receive, process, and display data representing the current values of such physiological parameters. Such embedded operating systems typically do not permit more than one program to execute on the physiological parameter display devices concurrently. In other words, such embedded operating systems do not allow multiple-program execution. As a result, the functionality of the physiological parameter display devices is constrained while the physiological parameter display devices are displaying data representing current values of physiological parameters of patients.

SUMMARY

A physiological parameter display device displays data representing the current values of one or more physiological parameters of a patient. The physiological parameter display device has an operating system that only allows a single program to operate at a given time. In addition, the program provides functionality that gives a user of the physiological parameter display device an ability to add new applications to the physiological parameter display device and/or run the new applications on the physiological parameter display device while the physiological parameter display device continues to display data representing current values of the one or more physiological parameters of the patient.

This summary is provided to introduce a selection of concepts. These concepts are further described below in the Detailed Description. This summary is not intended to identify key features or essential features of the claimed subject matter, nor is this summary intended as an aid in determining the scope of the claimed subject matter.

DETAILED DESCRIPTION

Figure 1:
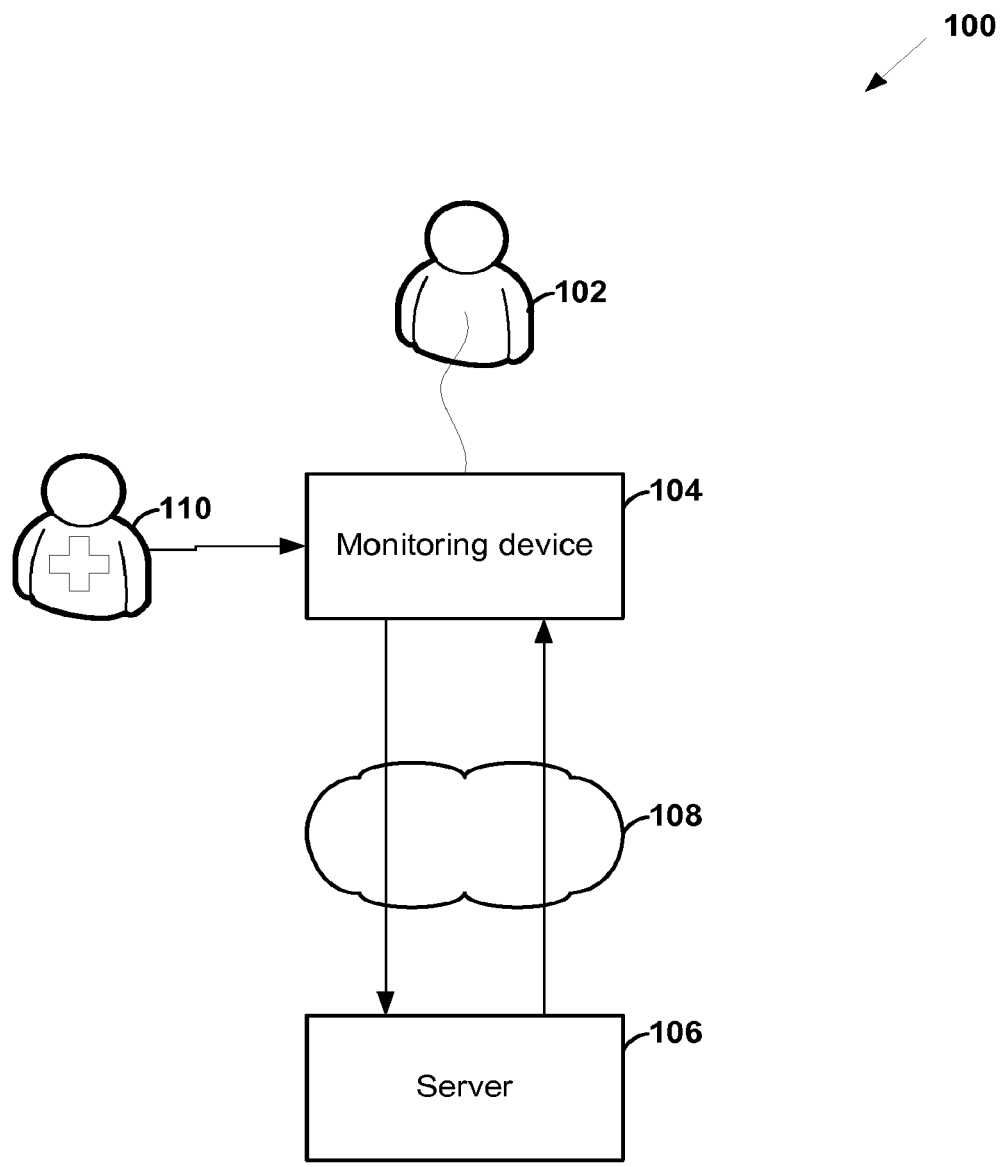
FIG. 1 is a block diagram illustrating an example system.

FIG. 1 is block diagram illustrating an example system 100. As illustrated in the example of FIG. 1, the system 100 comprises a patient 102, a monitoring device 104, a server 106, a network 108, and a user 110. It should be appreciated that in other embodiments, the system 100 can comprise additional people, devices, networks, and other components. For example, a different embodiment of the system 100 can comprise multiple monitoring devices and patients in communication via the network 108 with the server 106. Furthermore, the detailed description and the figures describe a monitoring device. The detailed description and figures can also be applicable to other classes of physiological parameter display devices, such as spot check devices.

The monitoring device 104 is a device that receives, on a continuing basis, signals indicative of current values of one or more physiological parameters of the patient 102. In various embodiments, the monitoring device 104 receives signals indicative of current values of various types of physiological parameters of the patient 102. For example, the physiological parameters can include a pulse rate of the patient 102, a blood pressure of the patient 102, a blood oxygen saturation level of the patient 102, a body temperature of the patient 102, a respiration rate of the patient 102, a neurological activity level of the patient 102, and other types of physiological parameters of the patient 102.

The monitoring device 104 can receive the signals from various types of sensors that are in wired or wireless communication with the monitoring device 104. For example, the monitoring device 104 can receive the signals from blood pressure cuffs, finger clips, thermometers, electrodes, and other types of sensors.

A program running on the monitoring device 104 processes the signals indicative of the current values of one or more physiological parameters and causes the monitoring device 104 to display data representative of current values of the physiological parameters. The user 110 monitors the physiological parameters of the patient 102 by reading the current values of the physiological parameters displayed by the monitoring device 104. For example, the program can process a signal indicative of the pulse rate of the patient 102 and can cause the monitoring device 104 to display current values of the pulse rate of the patient 102. In this way, the user 110 can monitor the current pulse rate of the patient 102.

The monitoring device 104 has an operating system. The operating system does not allow multiple-program execution. Multiple-program execution is a form of processing in which a processing unit works on multiple programs seemingly at the same time by parceling out the processing unit's time among the different programs. Because the operating system does not allow multiple-program execution, the operating system does not parcel out the processing unit's time among multiple programs. Effectively, the operating system only allows a single program to be running on the monitoring device 104 at any time. In other words, the operating system does not allow multiple programs to be running on the monitoring device 104 at one time.

Because the operating system only allows a single program to be running on the monitoring device 104 at any one time, the operating system can be less complex than an operating system that allows multiple programs to be running on the monitoring device at one time. However, because the operating system only allows a single program to be running on the monitoring device 104, the monitoring device 104 cannot run the program that causes the monitoring device 104 to display data representing current physiological parameters for the patient 102 while also running another program that provides some other functionality to the user 110. For example, the monitoring device 104 cannot run the program that causes the monitoring device to display parameters of the patient 102 while also running a separate program that provides a Body Mass Index (BMI) calculator.

As described in detail elsewhere in the document, a single program runs on the operating system. The program gives the user 110 an ability to install virtual applications on the monitoring device 104. In addition, the program gives the user 110 an ability to run the virtual applications on the monitoring device 104 while the monitoring device 104 continues to display data represent the current values of one or more physiological parameters of the patient 102. Because the program provides these abilities to the user 110, it can appear to the user 110 that the user 110 is able to add new applications to the monitoring device 104 and run these new applications on the monitoring device 104 while the monitoring device 104 continues to display data representing current values of one or more physiological parameters of the patient 102. The virtual applications include discrete sets of functionality provided by the monitoring device 104 to the user 110. The virtual applications are virtual in the sense that they are not separate programs operating on the monitoring device 104. For ease of explanation, such virtual applications are alternately referred to herein as "apps."

Figure 2:
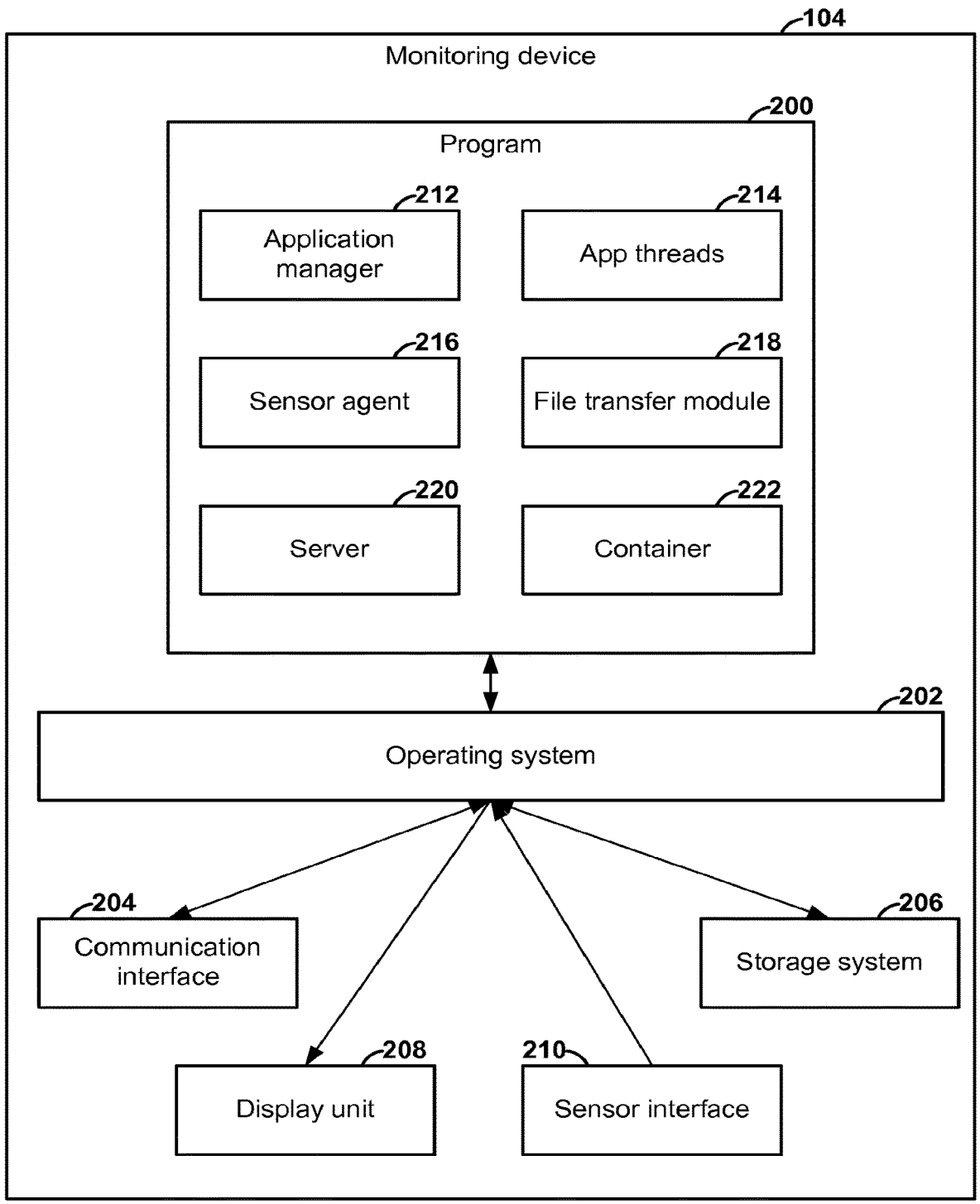
FIG. 2 is a block diagram illustrating example details of a monitoring device.

FIG. 2 is a block diagram illustrating example details of the monitoring device 104. In various embodiments, the monitoring device 104 can be a variety of different types of devices. For example, the monitoring device 104 can be a portable monitoring device, such as the Connex VSM® monitor manufactured by Welch Allyn, Inc. of Skaneateles, N.Y. In another example, the monitoring device 104 can be a wall mounted monitoring device. In yet another example, the monitoring device 104 can be a handheld monitoring device. In yet another example, the monitoring device 104 is an electrocardiograph, such as the CP 50™ electrocardiograph manufactured by Welch Allyn, Inc. of Skaneateles, N.Y.

As illustrated in the example of FIG. 2, the monitoring device 104 provides a program 200, an operating system 202, a communication interface 204, a storage system 206, a display unit 208, and a sensor interface 210. The communication interface 204 enables the monitoring device 104 to communicate with other devices via a network. The storage system 206 is a system of one or more computer-readable storage media that store data. The display unit 208 is a device for displaying information. The sensor interface 210 receives signals indicative of current values of physiological parameters from sensors.

The operating system 202 includes software that controls the allocation and usage of hardware resources of the monitoring device 104. Such hardware resources can include a central processing unit, memory, data storage devices, peripheral devices, and so on. The operating 202 only allows a single program to be running on the monitoring device 104 at one time. However, the operating system 202 allows multiple threads to be running within a program at one time. In some embodiments, it is not necessary for context switches to occur when multiple threads are operating concurrently.

In various embodiments, the operating system 202 can be various types of operating system. For instance, in some embodiments, the operating system 202 is a commercially available operating system, such as the ThreadX operating system manufactured by Express Logic, Inc. of San Diego, Calif.

The program 200 runs on the operating system 202. In other words, the operating system 202 starts the program 200 and manages how the program 200 uses resources of the monitoring device 104. The program 200 has multiple threads. As illustrated in the example of FIG. 2, the threads include an app manager 212, one or more app threads 214, a sensor agent 216, a file transfer module 218, a server 220, and a container 222.

The sensor agent 216 receives signals indicative of current values of one or more physiological parameters of the patient 102 from the sensor interface 210. The sensor agent 216 then processes the signals to cause the display unit 208 to display data representing current values of one or more physiological parameters of the patient 102. In addition, the sensor agent 216 can store data associated with the physiological parameters in the storage system 206.

The app manager 212 enables the user 110 to install apps on the monitoring device 104. In various embodiments, the app manager 212 enables the user 110 to install apps on the monitoring device 104 in various ways. For example, the app manager 212 can cause the display unit 208 to display an app installation interface. The app installation interface allows the user 110 to select apps to install on the monitoring device 104. In this example, the app installation interface comprises a list of available apps. In this example, the user 110 can install a given app by selecting the given app from the list of available apps.

When the app installation interface is displayed, the sensor agent 216 continues to process signals from the sensors and continues to cause the display unit 208 to display data representing the current values of the physiological parameters of the patient 102. However, the portion of the display unit 208 allocated to displaying the data representing the current values of the physiological parameters is reduced while the app installation interface is displayed. In this way, the user 110 can continue to monitor the physiological parameters of the patient 102 while the app installation interface is displayed.

When the user 110 selects an app to install, the file transfer module 218 communicates with the server 106 to retrieve app data associated with the selected app. The content of the app data differs in different embodiments and for different apps. For example, the app data for an app can comprise an icon, a set of parameters, and a script file. In another example, the app data for an app can comprise an icon, a set of parameters, and a set of Hypertext Markup Language (HTML) documents. After retrieving the app data for the selected app, the file transfer module 218 stores the app data for the selected app in the storage system 206. In some embodiments, the app data for an app can be used by computing devices other than monitoring devices to provide the functionality of the app. For example, a personal computer could use the app data for the app to provide the same functionality as when the monitoring device 104 uses the app data.

In addition, the app manager 212 enables the user 110 to start running apps that are installed on the monitoring device 104. In other words, the app manager 212 enables the user 110 to start providing the functionalities of the apps installed on the monitoring device 104. In various embodiments, the app manager 212 enables the user 110 to start running apps that are installed on the monitoring device 104 in various ways. For example, in some embodiments, the app manager 212 causes the display unit 208 to display an app selection interface. In this example, the app selection interface contains one or more controls associated with apps installed on the monitoring device 104. The user 110 can use these controls to select an app to run.

When the app selection interface is displayed, the sensor agent 216 continues to process signals from the sensors and continues to cause the display unit 208 to display data representing the current values of the physiological parameters of the patient 102. However, the portion of the display unit 208 allocated to displaying the data representing the current values of the physiological parameters is reduced while the app selection interface is displayed. In this way, the user 110 can continue to monitor the physiological parameters of the patient 102 while the app selection interface is displayed. In other embodiments, the display unit 208 does not display data representing the current values of the physiological parameters while the app selection interface is displayed.

When the user 110 selects an app to run, the app manager 212 provides an identifier of the selected app to the container 222. The container 222 is a thread that provides an environment in which the selected app runs. In various embodiments, the container 222 can be implemented in various ways. For example, the container 222 can be a web browser, such as Opera Mini or Opera Mobile. In another example, the container 222 can be multimedia platform, such as Adobe Flash.

The container 222 can run the selected app in various ways. For example, the container 222 can be a web browser and the identifier of the selected app can be a URL. In this example, the container 222 retrieves a resource, such as web page data, identified by the URL. The container 222 can retrieve the resource from various locations. For example, the container 222 can retrieve the resource from the server 220 operating at the monitoring device 104. In this example, the server 220 can retrieve the resource from the storage system 206 or dynamically generate the resource using data from the storage system 206 or another server. In another example, the container 222 can retrieve the resource from the server 106 via the network 108. In yet another example, the container 222 can retrieve the resource from a server other than the server 106 via the network 108.

When the container 222 receives the resource, the container 222 processes the resource. The container 222 processes different types of resources in different ways. For example, if the resource comprises HTML data, the container 222 renders the HTML data to present a web page on the display unit 208. In another example, if the resource comprises Adobe Flash data, the container 222 starts a Flash plug-in and provides the Flash data to the Flash plug-in.

Figure 3:
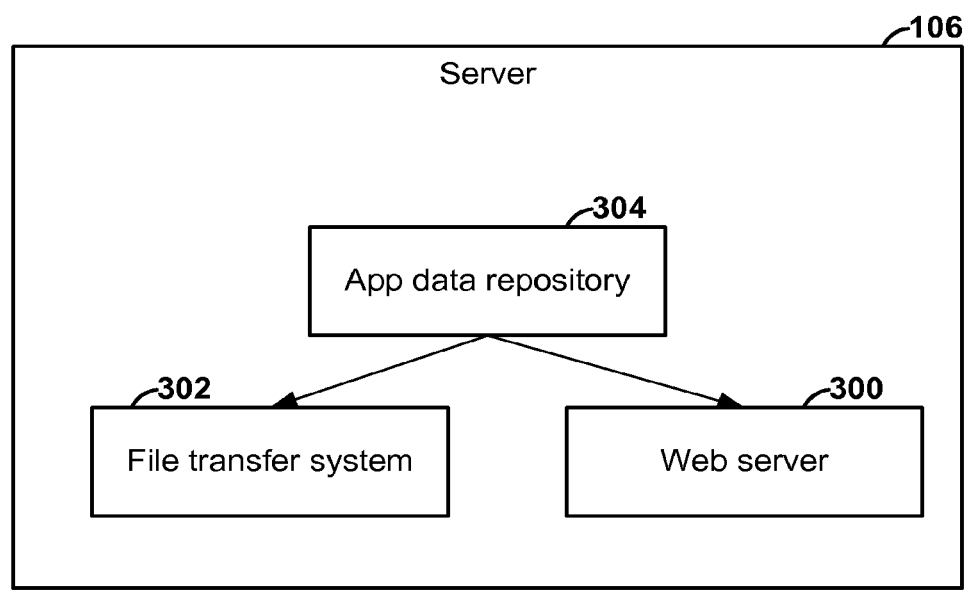
FIG. 3 is a block diagram illustrating example details of a server.

FIG. 3 is a block diagram illustrating example details of the server 106. As illustrated in the example of FIG. 3, the server 106 provides a web server 300 and a file transfer system 302. In addition, the server 106 provides an app data repository 304. In some embodiments, the server 106 provides the web server 300 and the file transfer system 302 by executing computer-executable instructions stored on one or more computer storage media. The server 106 stores the app data repository 304 on one or more computer storage media.

The web server 300 delivers content to client devices in response to requests from the client devices. For instance, the web server 300 can deliver web pages to the monitoring device 104 in response to requests sent by the monitoring device 104. In some instances, the web server 300 can deliver content by simply retrieving the content from one or more computer storage media attached to the server 106 and transmitting the content on the network 108. However, in other instances, the web server 300 can deliver content by dynamically generating the content and transmitting the content on the network 108. In various circumstances and embodiments, the web server 300 can dynamically generate content in various ways. For example, in some embodiments, the web server 300 can interact with one or more external systems to dynamically generate content. In this example, such external systems can include a variety of different types of systems, including Hospital Information Systems, Electronic Medical Record (EMR) systems, database systems, web services systems, and other types of systems that provide data.

The web server 300 is able to receive and respond to requests for a variety of different resources. For example, the web server 300 can respond to requests for web pages, Adobe Flash data, audio/video streams, available app lists, and so on. As discussed elsewhere in this specification, an available app list is a set of data that lists apps that are available to be installed on a monitoring device.

Furthermore, the web server 300 can receive requests for app data. When the web server 300 receives a request for app data for a particular app from a monitoring device, the web server 300 instructs the file transfer system 302 to send the app data to the monitoring device. In response, the file transfer system 302 retrieves the app data from the app data repository 304 and transmits the app data to the monitoring device. In various embodiments, the file transfer system 302 transmits the app data to the monitoring device in various ways. For example, the file transfer system 302 can transmit the app data to the monitoring device using HTTP, secure HTTP, the File Transfer Protocol (FTP), or another publicly-available communications protocol. In another example, the file transfer system 302 can transmit the app data to the monitoring device using a proprietary communications protocol, such as the Welch Allyn Communications Protocol (WACP).

Figure 4:
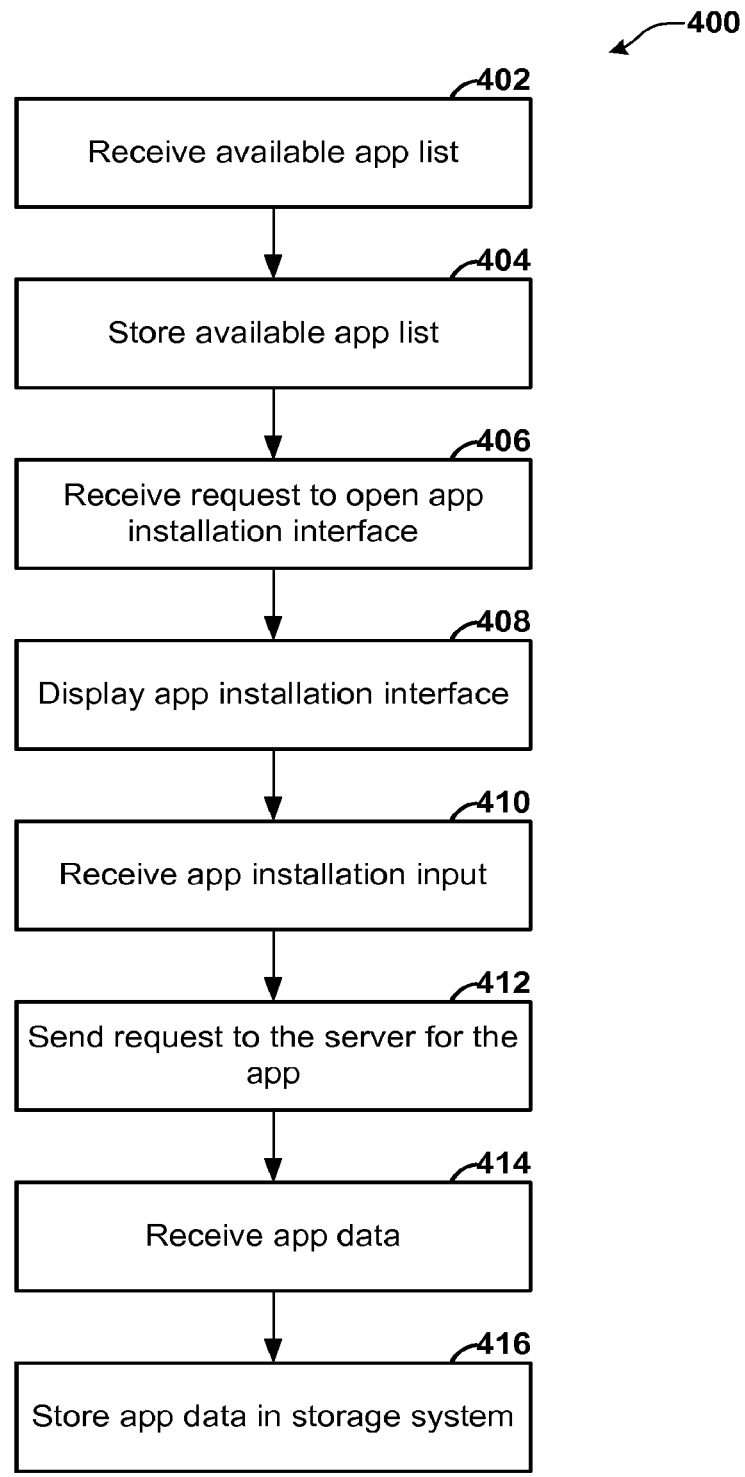
FIG. 4 is a flowchart illustrating an example operation to install an app on the monitoring device.

FIG. 4 is a flowchart illustrating all example operation 400 to install an app on the monitoring device 104. As illustrated in the example of FIG. 4, the operation 400 begins when the app manager 212 receives an available app list from the server 106 (402). The available app list comprises data that lists apps that are available to be installed on the monitoring device 104. The available app list can contain various details about the apps. For example, the available app list can contain names of apps, textual or graphical descriptions of apps, size requirements of apps, user comments or ratings regarding apps, and/or other types of details about the apps. After receiving the available app list, the app manager 212 stores the available app list in the storage system 206 (404).

Subsequently, the program 200 receives a request from the user 110 to open an app installation interface (406). In response, the app manager 212 causes the display unit 208 to display the app installation interface (408). The app installation interface contains information regarding at least some of the apps listed in the available app list. In some embodiments, the app manager 212 can provide search tools that allow the user 110 to provide search criteria to the app manager 212. In this example, the app installation interface lists available apps that are responsive to the search criteria provided by the user 110. When the app installation interface is displayed, the monitoring device 104 continues to display current data representing the current values of the physiological parameters of the patient 102.

Next, the app manager 212 receives app installation input from the user 110 via the app installation interface (410). The app installation input is a request by the user 110 to install an app on the monitoring device 104. The app manager 212 receives the app installation input when the user 110 selects the app from the list of available apps displayed in the app installation interface.

In response to receiving the app installation input from the user 110, the app manager 212 sends a request to the server 106 for app data for the selected app (412). Subsequently, the app manager 212 receives the app data for the selected app (414). After receiving the app data for the selected app, the app manager 212 stores the app files for the selected app in the storage system 206 (416). In some embodiments, the user 110 may need to agree to a license before receiving the app data or before running the selected app. The license may be from a developer of the selected app and/or from a distributor of the selected app (i.e., an entity operating the server 106).

Figure 5:
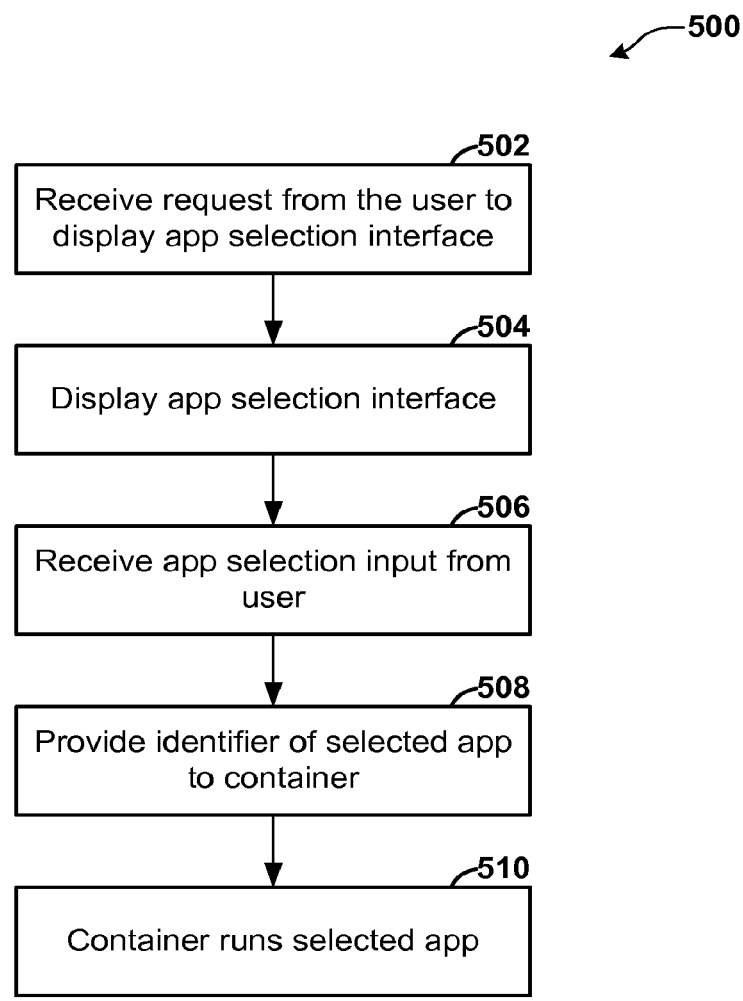
FIG. 5 is a flowchart illustrating an example operation to run an app.

FIG. 5 is a flowchart illustrating an example operation 500 to run an app. As illustrated in the example of FIG. 5, the operation 500 begins when the program 200 receives a request from the user 110 to display an app selection interface (502). In response to the request to display the app selection interface, the app manager 212 causes the display unit 208 to display the app selection interface (504). The app selection interface comprises controls associated with apps installed on the monitoring device 104. In various embodiments, the controls in the app selection interface can have various forms. For example, the controls in the app selection interface can comprise selectable icons. In this example, the downloaded app data for the installed apps include the icons. The app manager 212 retrieves the icons from the storage system 206 when the app manager 212 generates the app selection interface. In another example, the controls in the app selection interface can comprise selectable icons with textual titles. In yet another example, the controls in the app selection interface can comprise textual descriptions of installed apps with associated radio button controls.

Figure 6:
FIG. 6 is a screen illustration of an example app selection interface.

FIG. 6 is a screen illustration of an example app selection interface 600. The app selection interface 600 is a user interface displayed by the display unit 208 of the monitoring device 104. As illustrated in the example of FIG. 6, the app selection interface 600 comprises a parameter pane 602. The parameter pane 602 contains data representing current values of physiological parameters of the patient 102. In the example of FIG. 6, the parameter pane 602 includes data representing the current values of the systolic and diastolic blood pressures of the patient 102, the blood oxygen saturation of the patient 102, the pulse rate of the patient 102, and the body temperature of the patient 102.

In addition to the parameter pane 602, the app selection interface 600 comprises an app selection pane 604. The app selection pane 604 contains icons 606 associated with apps installed on the monitoring device 104. The app selection pane 604 also includes a scroll bar 608. When the app selection pane 604 does not have enough space to show the icons associated with all of the apps installed on the monitoring device 104, the user 110 can use the scroll bar 608 to cause the app selection pane 604 to reveal icons associated with additional apps. In the example of FIG. 6, the user 110 can provide app selection input to the app manager 212 by touching one of the icons 606.

Reference is now made again to FIG. 5. When the app selection interface is displayed, the app manager 212 receives an app selection input from the user 110 via the app selection interface (506). The app selection input indicates one of the installed apps. In various embodiments, the app manager 212 receives the app selection input in various ways. For example, in embodiments where the app selection interface comprises selectable icons associated with installed apps, the app manager 212 can receive the app selection input when the user 110 selects one of the icons. In another example, in embodiments where the app selection interface comprises radio button controls associated with installed apps, the app manager 212 receives the app selection input when the user 110 selects one of the radio button controls and then selects a submit button.

In response to receiving the app selection input, the app manager 212 provides an identifier of the selected app to the container 222 (508). In various embodiments, the app manager 212 provides the identifier of the selected app to the container 222 in various ways. For example, in some embodiments, the container 222 can be a web browser and the identifier of the selected app can be a URL. In this example, the app manager 212 provides the URL to the web browser.

After the app manager 212 provides the identifier of the selected app to the container 222, the container 222 runs the selected app (510). When the container 222 runs the selected app, the container 222 causes the display unit 208 to display an app interface. The app interface contains text, images, video, or other information belonging to one or more apps. In some embodiments in which the container 222 is a web browser, the app interface does not include conventional web navigation controls, such as a back button, a forward button, a home button, a reload button, an address bar, and so on. Consequently, it may appear to the user that the monitoring device 104 is running the selected app natively. Because the user 110 is not provided with any indication that the selected app is running through a web browser, it may appear to the user 110 like the selected app is actually running as a separate application on the monitoring device 104.

Furthermore, when the app interface is displayed, the monitoring device 104 continues to display current data representing the physiological parameters of the patient 102. The monitoring device 104 is able to continue displaying current parameter data of the patient 102 because the sensor agent 216 and the container 222 execute as separate threads. In other embodiments, the display unit 208 does not display data representing the current values of the physiological parameters while the app interface is displayed.

The container 222 runs various types of apps in various ways. For example, the container 222 can be a web browser and the selected app can comprise a set of web pages. In this example, the container 222 runs the selected app by requesting the HTML documents from a server, such as the server 220 or the web server 300. In this example, the HTML documents can be static or dynamically-generated web pages. Upon receiving the HTML documents, the container 222 renders the HTML documents in the app interface. Furthermore, in this example, the HTML documents can contain embedded scripts, such as JavaScript scripts or VBScript scripts. The container 222 can process these embedded scripts as part of rendering the web pages and/or after the container 222 renders such web pages.

In another example, the container 222 runs the selected app by requesting Extensible Markup Language (XML) documents from a server, such as the server 220 or the web server 300. The container 222 processes the XML documents to cause the app interface to contain various elements.

In yet another example, the container 222 is a Flash player. In this example, the container 222 runs the selected app by retrieving a Flash file from a server, such as the server 220 or the web server 300. The container 222 then processes the Flash file to display various elements in the app interface.

In yet another example, the container 222 is a script interpreter. In this example, the container 222 runs the selected app by requesting one or more scripts from a server, such as the server 220 or the web server 300, or by requesting one or more scripts from the storage system 206. Upon receiving the one or more scripts, the container 222 interprets the scripts and performs the commands indicated by the scripts. As part performing the commands indicated by the scripts, the container 222 can initialize and start one or more of the app threads 214. The app threads 214 operate within the program 200. The app threads 214 can provide various functionalities. For example, one of the app threads 214 can process a physiological parameter of the patient and update a chart on an ongoing basis.

In yet another example, the container 222 is an execution environment for binary executable files. For instance, the app data can include compiled Java file and the container 222 can be a Java Virtual Machine. In another instance, the app data can include one or more compiled .NET assemblies and the container 222 can be a Common Language Runtime.

Figure 7:
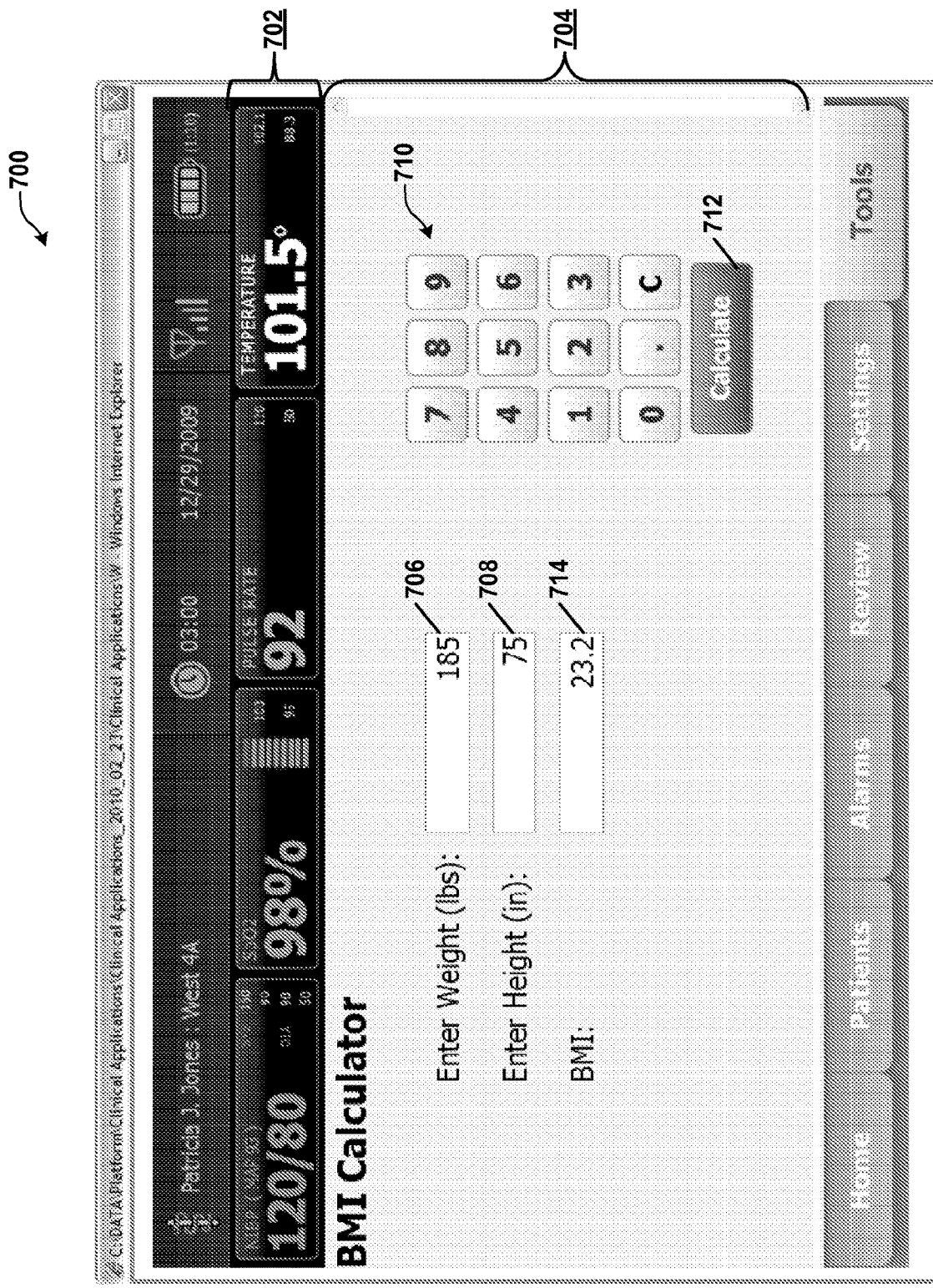
FIG. 7 is a screen illustration of an example user interface of a first app running on the monitoring device.

FIG. 7 is a screen illustration of an example user interface 700 of a first app running on the monitoring device 104. The user interface 700 is a user interface displayed by the display unit 208 of the monitoring device 104. In some embodiments, the monitoring device 104 displays the user interface 700 when the user 110 selects one of the icons 606 from the app selection interface 600.

As illustrated in the example of FIG. 7, the user interface 700 comprises a parameter pane 702. The parameter pane 702 contains data representing current values of physiological parameters of the patient 102. In the example of FIG. 7, the parameter pane 702 includes data representing the current values of systolic and diastolic blood pressures of the patient 102, the blood oxygen saturation of the patient 102, the pulse rate of the patient 102, and the body temperature of the patient 102.

In addition to the parameter pane 702, the user interface 700 contains an app pane 704. The app pane 704 contains user interface elements that are specific to an app. The app pane 704 contains a weight control 706 and a height control 708. The weight control 706 and the height control 708 allow the user 110 to enter a weight and a height. The app pane 704 also includes numeric keypad controls 710 that allow the user 110 to enter numbers into the weight control 706 and the height control 708. The app pane 704 also includes a calculate control 712. When the user 110 has entered numbers into the weight control 706 and the height control 708 and the user 110 selects the calculate control 712, a body mass index (BMI) is displayed in a BMI control 714 in the app pane 704.

Figure 8:
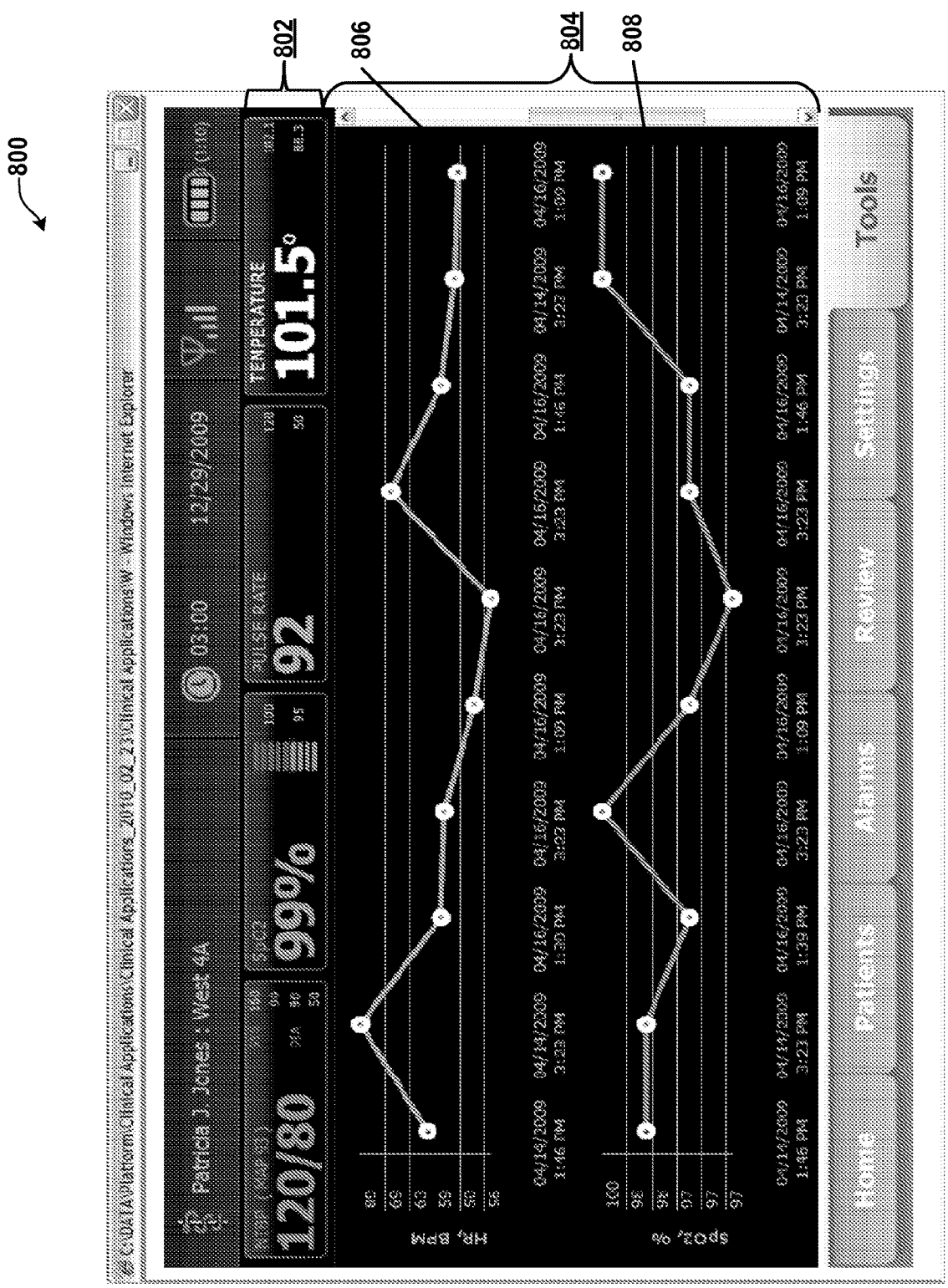
FIG. 8 is a screen illustration of an example user interface of a second app running on the monitoring device.

FIG. 8 is a screen illustration of a user interface 800 of a second app running on the monitoring device 104. The user interface 800 is a user interface displayed by the display unit 208 of the monitoring device 104. In some embodiments, the monitoring device 104 displays the user interface 800 when the user 110 selects one of the icons 606 from the app selection interface 600.

As illustrated in the example of FIG. 8, the user interface 800 comprises a parameter pane 802. The parameter pane 802 contains data representing current values of physiological parameters of the patient 102. In the example of FIG. 8, the parameter pane 802 contains data representing current the current values of systolic and diastolic blood pressures of the patient 102, the blood oxygen saturation of the patient 102, the pulse rate of the patient 102, and the body temperature of the patient 102.

In addition to the parameter pane 802, the user interface 800 contains an app pane 804. The app pane 804 contains user interface elements that are specific to an app. The app pane 804 comprises a pulse rate chart 806 and a blood oxygen saturation chart 808. The pulse rate chart 806 shows readings of the pulse rate of the patient 102 over time. The blood oxygen saturation chart 808 shows readings of the blood oxygen saturation of the patient 102 over time. The second app can dynamically generate the pulse rate chart 806 and the blood oxygen saturation chart 808 using data generated by sensors attached to the monitoring device 104, data retrieved from the server 220, data retrieved from the web server 300, and/or using data retrieved from another source.

Figure 9:
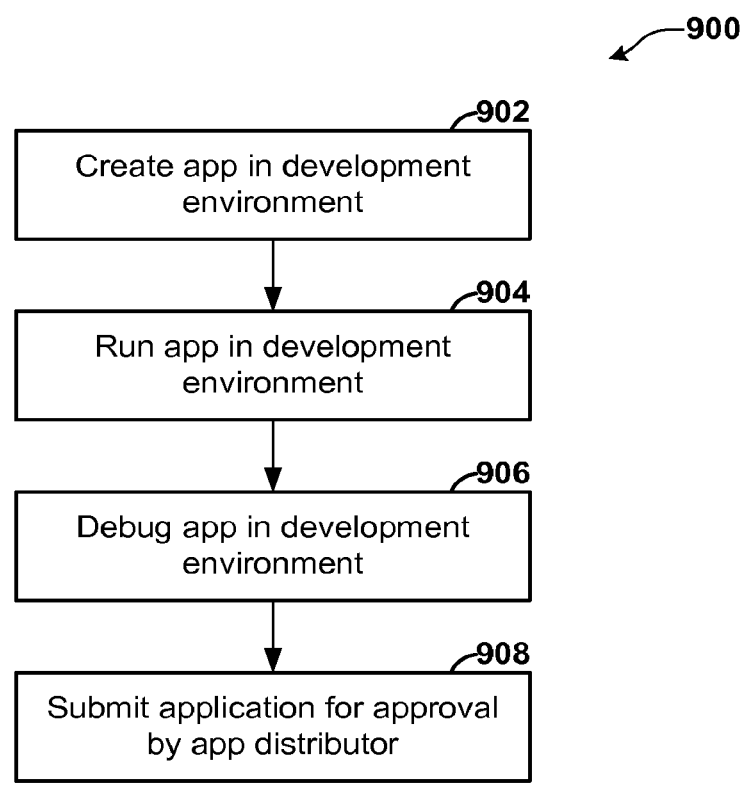
FIG. 9 is a flowchart illustrating an example operation to develop an app.

FIG. 9 is a flowchart illustrating an example operation 900 to develop an app that can run on the monitoring device 104. As illustrated in the example of FIG. 9, a developer can first develop the app in a development environment (902). The development environment is a set of one or more computers used by the developer to develop apps. Monitoring devices used by the end users cannot retrieve app data from the development environment.

After initially developing the app, the developer runs the app using the development environment (904). Running the app using the development environment provides the developer with an opportunity to determine whether the app is functioning correctly. After running the app using the development environment, the developer debugs the app using the development environment (906). Debugging the app can include editing software code, modifying HTML or XML files, editing graphics or other media, and other tasks to ensure the app provides the correct functionality. The developer can iterate through the process of running the app and debugging the app in the development environment multiple times.

When the developer is satisfied with the functionality and appearance of the app, the developer submits the app for approval by an app distributor (908). The app distributor is an entity that is responsible for controlling which apps are available to be installed on monitoring devices. In various embodiments, the app distributor can be various types of entities. For example, the app distributor can be an enterprise that manufactures monitoring devices. In another example, the app distributor can be an entity that operates the server 106.

Upon receiving the app from the developer, the app distributor conducts an approval process to determine whether the app should be allowed to be installed on monitoring devices. If the app distributor approves the app, the app becomes available for installation on monitoring devices, such as the monitoring device 104. If the app distributor rejects the app, the app distributor notifies the developer and can inform the developer why the app distributor did not approve the app. The app distributor can reject the app for a variety of reasons. For example, the app distributor can reject the app if the app does not function properly, poses a security risk, contains inappropriate content, or if the app does not meet various other criteria.

Figure 10:
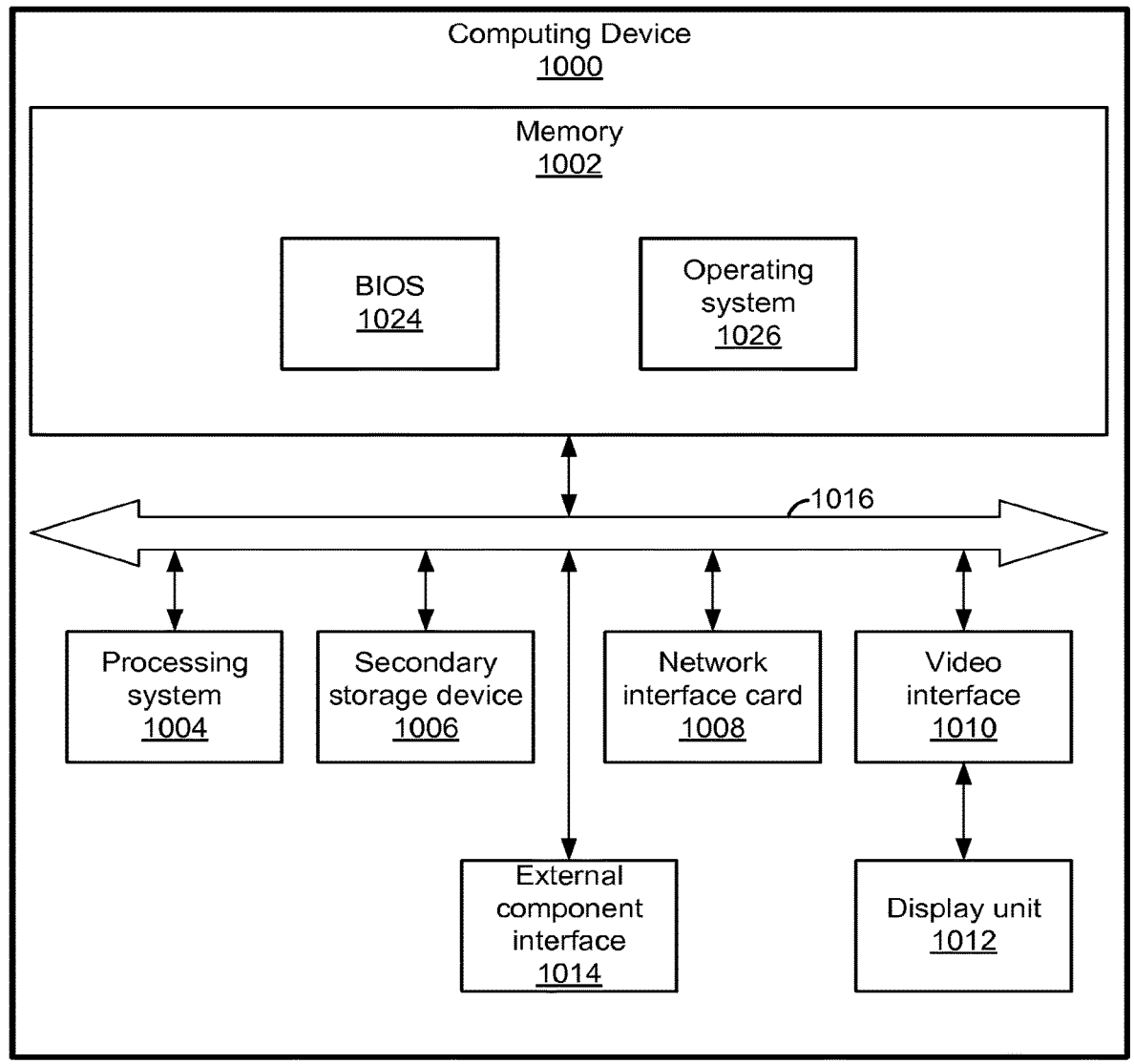
FIG. 10 is a block diagram illustrating an example computing device.

FIG. 10 is a block diagram illustrating an example computing device 1000. In some embodiments, the monitoring device 104 and/or the server 106 are implemented using one or more computing devices like the computing device 1000. It should be appreciated that in other embodiments, the monitoring device 104 and/or the server 106 are implemented using computing devices having hardware components other than those illustrated in the example of FIG. 10.

In different embodiments, computing devices are implemented in different ways. For instance, in the example of FIG. 10, the computing device 1000 comprises a memory 1002, a processing system 1004, a secondary storage device 1006, a network interface card 1008, a video interface 1010, a display unit 1012, an external component interface 1014, and a communication medium 1016. In other embodiments, computing devices are implemented using more or fewer hardware components. For instance, in another example embodiment, a computing device does not include a video interface, a display unit, an external storage device, or an input device.

The term computer readable media as used herein may include computer storage media. Computer storage media may include volatile and nonvolatile, removable and non-removable media implemented in any method or technology for storage of information, such as computer readable instructions, data structures, program modules, or other data. The memory 1002 includes one or more computer storage media capable of storing data and/or instructions. As used in this document, a computer storage medium is a device or article of manufacture that stores data and/or software instructions readable by a computing device. In different embodiments, the memory 1002 is implemented in different ways. For instance, in various embodiments, the memory 1002 is implemented using various types of computer storage media. Example types of computer storage media include, but are not limited to, dynamic random access memory (DRAM), double data rate synchronous dynamic random access memory (DDR SDRAM), reduced latency DRAM, DDR2 SDRAM, DDR3 SDRAM, Rambus RAM, solid state memory, flash memory, read-only memory (ROM), electrically-erasable programmable ROM, and other types of devices and/or articles of manufacture that store data.

The term computer readable media as used herein may also include communication media. Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

The processing system 1004 includes one or more physical integrated circuits that selectively execute software instructions. In various embodiments, the processing system 1004 is implemented in various ways. For example, the processing system 1004 can be implemented as one or more processing cores. In this example, the processing system 1004 can comprise one or more Intel Core 2 microprocessors. In another example, the processing system 1004 can comprise one or more separate microprocessors. In yet another example embodiment, the processing system 1004 can comprise an ASIC that provides specific functionality. In yet another example, the processing system 1004 provides specific functionality by using an ASIC and by executing software instructions. In another example, the processing system 1004 is an ARM7 processor. In different embodiments, the processing system 1004 executes software instructions in different instruction sets. For example, the processing system 1004 executes software instructions in instruction sets such as the x86 instruction set, the POWER instruction set, a RISC instruction set, the SPARC instruction set, the IA-64 instruction set, the MIPS instruction set, and/or other instruction sets.

The secondary storage device 1006 includes one or more computer storage media. The secondary storage device 1006 stores data and software instructions not directly accessible by the processing system 1004. In other words, the processing system 1004 performs an I/O operation to retrieve data and/or software instructions from the secondary storage device 1006. In various embodiments, the secondary storage device 1006 is implemented by various types of computer-readable data storage media. For instance, the secondary storage device 1006 may be implemented by one or more magnetic disks, magnetic tape drives, CD-ROM discs, DVD-ROM discs, Blu-Ray discs, solid state memory devices, Bernoulli cartridges, and/or other types of computer-readable data storage media.

The network interface card 1008 enables the computing device 1000 to send data to and receive data from a communication network. In different embodiments, the network interface card 1008 is implemented in different ways. For example, in various embodiments, the network interface card 1008 is implemented as an Ethernet interface, a token-ring network interface, a fiber optic network interface, a wireless network interface (e.g., WiFi, WiMax, etc.), or another type of network interface.

The video interface 1010 enables the computing device 1000 to output video information to the display unit 1012. In different embodiments, the video interface 1010 is implemented in different ways. For instance, in one example embodiment, the video interface 1010 is integrated into a motherboard of the computing device 1000. In another example embodiment, the video interface 1010 is a video expansion card. In various embodiments, the display unit 1012 can be a cathode-ray tube display, an LCD display panel, a plasma screen display panel, a touch-sensitive display panel, an LED screen, a projector, or another type of display unit. In various embodiments, the video interface 1010 communicates with the display unit 1012 in various ways. For example, the video interface 1010 can communicate with the display unit 1012 via a Universal Serial Bus (USB) connector, a VGA connector, a digital visual interface (DVI) connector, an S-Video connector, a High-Definition Multimedia Interface (HDMI) interface, a DisplayPort connector, or another type of connection.

The external component interface 1014 enables the computing device 1000 to communicate with external devices. In various embodiments, the external component interface 1014 is implemented in different ways. For example, the external component interface 1014 can be a USB interface, a FireWire interface, a serial port interface, a parallel port interface, a PS/2 interface, and/or another type of interface that enables the computing device 1000 to communicate with external devices. In different embodiments, the external component interface 1014 enables the computing device 1000 to communicate with different external components. For example, the external component interface 1014 can enable the computing device 1000 to communicate with external storage devices, input devices, speakers, phone charging jacks, modems, media player docks, other computing devices, scanners, digital cameras, a fingerprint reader, and other devices that can be connected to the computing device 1000. Example types of external storage devices include, but are not limited to, magnetic tape drives, flash memory modules, magnetic disk drives, optical disc drives, flash memory units, zip disk drives, optical jukeboxes, and other types of devices comprising one or more computer storage media. Example types of input devices include, but are not limited to, keyboards, mice, trackballs, stylus input devices, key pads, microphones, joysticks, touch-sensitive display screens, and other types of devices that provide user input to the computing device 1000.

The communications medium 1016 facilitates communication among the hardware components of the computing device 1000. In different embodiments, the communications medium 1016 facilitates communication among different components of the computing device 1000. For instance, in the example of FIG. 10, the communications medium 1016 facilitates communication among the memory 1002, the processing system 1004, the secondary storage device 1006, the network interface card 1008, the video interface 1010, and the external component interface 1014. In different implementations of the computing device 1000, the communications medium 1016 is implemented in different ways. For instance, in different implementations of the computing device 1000, the communications medium 1016 may be implemented as a PCT bus, a PCT Express bus, an accelerated graphics port (AGP) bus, an Infiniband interconnect, a serial Advanced Technology Attachment (ATA) interconnect, a parallel ATA interconnect, a Fiber Channel interconnect, a USB bus, a Small Computing system Interface (SCSI) interface, or another type of communications medium.

The memory 1002 stores various types of data and/or software instructions. For instance, in the example of FIG. 10, the memory 1002 stores a Basic Input/Output System (BIOS) 1024, and an operating system 1026. The BIOS 1024 includes a set of software instructions that, when executed by the processing system 1004, cause the computing device 1000 to boot up. The operating system 1026 includes a set of software instructions that, when executed by the processing system 1004, cause the computing device 1000 to provide an operating system that coordinates the activities and sharing of resources of the computing device 1000.

The various embodiments described above are provided by way of illustration only and should not be construed as limiting. Those skilled in the art will readily recognize various modifications and changes that may be made without following the example embodiments and applications illustrated and described herein. For example, the operations shown in the figures are merely examples. In various embodiments, similar operations can include more or fewer steps than those shown in the figures. Furthermore, in other embodiments, similar operations can include the steps of the operations shown in the figures in different orders.

What is claimed is:

1. A patient monitoring device, comprising:
a processing unit;
a display unit; and
memory storing instructions that, when executed by the processing unit, cause the patient monitoring device to:
execute one operating system that only supports single-program execution; and
execute a single program that runs on the one operating system, the single program providing functionality to:
receive at least one physiological parameter signal of a patient;
display a parameter pane on the display unit in an expanded view, wherein the parameter pane comprises data representing a current value of a physiological parameter associated with the at least one physiological parameter signal;
install and execute multiple applications on the one operating system of the patient monitoring device;
receive a user request to display on the display unit an app selection interface while displaying the parameter pane in the expanded view;
display the app selection interface in response to the user request, the app selection interface comprising:
the parameter pane, displayed in a first portion of the display unit, contains the data representing the current value of the physiological parameter of the patient in a reduced view;
an app selection pane, displayed in a second portion of the display unit, that contains icons associated with the multiple applications installed on the patient monitoring device and controls that cause one of the multiple applications to run on the patient monitoring device, each application operating within the single program; and
run at least one of the multiple applications in response to selection of an app from the app selection pane and display an app interface in the second portion of the display unit on the one operating system of the patient monitoring device while the patient monitoring device continues to display data representing the current value of the physiological parameter in the first portion of the display unit, wherein the applications are discrete sets of functionality provided by the patient monitoring device to a user.

2. The patient monitoring device according to claim 1, wherein the single program additionally provides functionality to: receive an available app list from a server, the available app list including data listing apps that are available to be installed on the patient monitoring device; cause the display unit to display an app installation interface; receive app installation input including a selected app, wherein the display unit continues to display the current value of the physiological parameter; and send a request to the server for app data for the selected app.

3. The patient monitoring device according to claim 2, wherein the single program additionally provides functionality to: receive the app data for the selected app, the app data including app files; store the app files in the memory; and determine whether the selected app requires a license agreement.

4. The patient monitoring device according to claim 1, wherein the single program additionally provides functionality to: receive an app selection input via the app selection interface, the app selection input indicating a given application; and using a thread within the single program to run the given application.

5. The patient monitoring device according to claim 1, wherein the physiological parameter is one of the following: blood pressure, blood oxygen saturation, pulse rate, and body temperature.

6. The patient monitoring device according to claim 4, wherein the single program additionally provides functionality to: store app data for the given application in the memory; and run a container thread within the single program, the container thread running the given application by processing the app data for the given application.

7. The patient monitoring device according to claim 6, wherein the container thread comprises at least one of: a web browser, a multimedia platform, a script interpreter, and an execution environment for binary executable files.

8. The patient monitoring device according to claim 7, wherein to run the given application, the container thread retrieves data from the server.

9. The patient monitoring device according to claim 8, wherein the single program additionally provides functionality to: run the server as a thread within the single program.

10. The patient monitoring device according to claim 9, wherein the container thread starts the thread for the given application when the container thread processes the app data for the given application.

11. A method implemented on a physiological parameter display device, the method comprising:
   executing one operating system that only allows a single program to be executed; and
   executing the single program that runs on the one operating system, the single program providing functionality to:
      receive at least one physiological parameter signal of a patient;
      display a parameter pane on a display unit of the physiological parameter display device, wherein the parameter pane comprises data representing a current value of a physiological parameter associated with the at least one physiological parameter signal, the parameter pane being displayed in an expanded view;
      receive a user request to display an app selection interface while displaying the parameter pane in the expanded view,
      display the app selection interface in response to the user request, wherein the app selection interface allows a user to select applications to install and execute on the one operating system of the physiological parameter display device, the app selection interface including the parameter pane and an app selection pane,
         wherein the parameter pane, displayed in a first portion of the display unit, includes a display of the current physiological parameter data in a reduced view, and
         wherein the app selection pane, displayed in a second portion of the display unit, includes selectable icons, with each of the selectable icons having controls that cause one of the applications to be run on the one operating system of the physiological parameter display device, each application operating within the single program;
      run at least one of the multiple applications in response to selection of an app from the app selection pane and display an app interface in the second portion of the display unit on the one operating system of the patient monitoring device while the patient monitoring device continues to display data representing the current value of the physiological parameter in the first portion of the display unit, wherein the applications are discrete sets of functionality provided by the patient monitoring device to a user.

12. The method according to claim 11, wherein executing the single program further provides functionality to: provide an app installation interface; install the applications on the physiological parameter display device; and run the applications on the physiological parameter display device while the physiological parameter display device continues to display data representing a current value of the physiological parameter, wherein the applications are discrete sets of functionality provided by the physiological parameter display device to the user; and wherein each application operates within the single program.

13. The method according to claim 12, wherein executing the single program further provides functionality to: receive app installation input from the user via the app installation interface, the app installation input being a request by the user to install a given application on the physiological parameter display device; in response to receiving the app installation input, send a request to a server for app data for the given application; receive the app data for the given application; and store the app data for the given application in a storage system at the physiological parameter display device.

14. The method according to claim 12, wherein the applications include a given application; wherein the method further comprises: storing app data for the given application in a storage system at the physiological parameter display device; and wherein executing the single program comprises: running a container thread within the single program, the container thread running the given application by processing the app data for the given application.

15. The method according to claim 14, wherein the container thread comprises at least one of: a web browser, a multimedia platform, a script interpreter, and an execution environment for binary executable files.

16. The method according to claim 14, wherein to run the given application, the container thread retrieves data from a server; and wherein executing the single program further comprises running the server as a thread within the single program.

17. The method according to claim 14, wherein the container thread starts the thread for the given application when the container thread processes the app data for the given application.

18. A physiological parameter display device, comprising:
   a processing unit;
   a display unit; and
   memory storing instructions that, when executed by the processing unit, cause the patient monitoring device to:
      execute one operating system that allows only single-program execution; and
      execute a single program that runs on the one operating system, the single program providing functionality to:
         receive at least one physiological parameter signal of a patient;
         display a parameter pane on the display unit in an expanded view, wherein the parameter pane comprises data representing a current value of a physiological parameter associated with the at least one physiological parameter signal;
         install and execute multiple applications on the one operating system of the physiological parameter display device;
         receive a user request while displaying the parameter pane in the expanded view causing the display unit of the physiological parameter display device to display an app selection interface, the app selection interface including the parameter pane and an app selection pane,
         wherein the parameter pane, displayed in a first portion of the display unit, includes a display of current physiological parameter data in a reduce view;
         wherein the app selection pane, displayed in a second portion of the display unit, includes selectable icons, with each of the selectable icons having controls that cause one of the applications to be run on the one operating system of the physiological parameter display device, each application operating within the single program; and
         run at least one of the multiple applications in response to selection of an app from the app selection pane and display an app interface in the second portion of the display unit on the one operating system of the physiological parameter display device while the physiological parameter display device continues to display data representing the current value of the physiological parameter in the first portion of the display unit, wherein the applications are discrete sets of functionality provided by the patient monitoring device to a user.

19. The patient monitoring device according to claim 1, wherein the app selection pane includes a scroll bar allowing the user to cause the app selection pane to reveal icons associated with additional apps when the app selection pane does not have enough space to show icons associated with all of the apps installed on the patient monitoring device.

* * * * *